United States Patent [19]

Buchholtz

[11] Patent Number: 5,305,731
[45] Date of Patent: Apr. 26, 1994

[54] APPARATUS FOR GENERATING ACOUSTIC WAVE HAVING A LIQUID LENS WITH AN ADJUSTABLE FOCAL LENGTH

[75] Inventor: Gerhard Buchholtz, Erlangen, Fed. Rep. of Germany

[73] Assignee: Siemens Aktiengesellschaft, Munich, Fed. Rep. of Germany

[21] Appl. No.: 959,631

[22] Filed: Oct. 13, 1992

[30] Foreign Application Priority Data

Oct. 31, 1991 [DE] Fed. Rep. of Germany ....... 4136004

[51] Int. Cl.⁵ .............................................. A61B 17/22
[52] U.S. Cl. ................................... 601/4; 128/663.01; 128/660.03; 367/150; 367/151; 601/2
[58] Field of Search ........ 128/24 EL, 24 AA, 660.03, 128/663.01; 367/175, 150, 151, 166

[56] References Cited

U.S. PATENT DOCUMENTS

| | | |
|---|---|---|
| 4,697,588 | 10/1987 | Reichenberger . |
| 4,718,421 | 1/1988 | Rohwedder et al. . |
| 4,838,248 | 6/1989 | Grasser ........................... 128/24 EL |
| 4,844,079 | 7/1989 | Naser et al. ...................... 128/24 EL |
| 4,928,672 | 5/1990 | Grasser et al. . |
| 4,977,888 | 12/1990 | Rietter et al. . |
| 5,009,232 | 4/1991 | Hassler et al. .................. 128/24 EL |

FOREIGN PATENT DOCUMENTS

| | | |
|---|---|---|
| 0131654 | 1/1985 | European Pat. Off. ....... 128/24 EL |
| 3727692 | 3/1989 | Fed. Rep. of Germany ... 128/24 EL |
| 3739393 | 6/1989 | Fed. Rep. of Germany . |
| 179076 | 3/1966 | U.S.S.R. . |

Primary Examiner—Lee S. Cohen
Assistant Examiner—Brian L. Casler
Attorney, Agent, or Firm—Hill, Steadman & Simpson

[57] ABSTRACT

A generator for acoustic waves has a source of acoustic waves with which acoustic waves can be introduced into an acoustic propagation medium and a liquid lens having a variable focal length which is arranged in the acoustic propagation medium, the liquid lens having two lens walls and a lens liquid situated therebetween. At least one of the lens walls is deformable for the purpose of varying the focal length. The liquid lens has a central opening, so that the lens walls have an outer and an inner edge, and the outer edge of the deformable lens wall is fixed and the inner edge is displaceable in the direction of the center axis of the liquid lens for the purpose of varying the focal length.

11 Claims, 2 Drawing Sheets

APPARATUS FOR GENERATING ACOUSTIC WAVE HAVING A LIQUID LENS WITH AN ADJUSTABLE FOCAL LENGTH

BACKGROUND OF THE INVENTION

1. Field of the Invention

The present invention is directed to an apparatus for generating acoustic waves of the type having a liquid lens for focusing the acoustic waves.

2. Description of the Prior Art

Generators for generating acoustic waves are known which include a source of acoustic waves with which the acoustic waves can be introduced into an acoustic propagation medium, and a variable focal length liquid lens arranged in the acoustic propagation medium. The liquid lens has two lens walls and a lens liquid situated therebetween and it is known to employ means for deforming at least one of the lens walls for the purpose of varying the focal length.

Such generators, for example can be designed as pressure pulse generators for medical purposes, for example for treating stone pathologies (lithotripsy), tumors or bone conditions (osteorestoration). Such generators, moreover, can be designed as pressure pulse generators utilized in testing materials, with which specimens of material are charged with pressure pulses. Further, such generators can be designed as medical ultrasound generators for diagnostic purposes (for example, ultrasound imaging) or therapeutic purposes (for example, hyperthermia) as well as other types ultrasound generators that serve the purpose, for example, of testing materials or other purposes. In all cases, the acoustic propagation medium serves the purpose of conducting the generated acoustic waves from the source of acoustic waves in the direction of the subject to be acoustically irradiated. The generator and the subject to be acoustically irradiated must be aligned relative to one another such that the specific region of the subject to be acoustically irradiated is situated in the focal region of the acoustic waves, i.e. in the focal region of the liquid lens. The focal length of the liquid lens can be varied in order to be able to match the distance of the focal region of the acoustic waves from the surface of the subject to be acoustically irradiated to the respective requirements. German Published Application 37 39 393 discloses a generator fashioned as a medical pressure pulse generator, namely as a lithotriptor. In the case of the known generator, the means for deforming at least one lens wall are fashioned as a mechanical adjustment device that has a complicated structure and tends to malfunction under certain circumstances. A solution disclosed by German Utility Model 85 23 024, corresponding to U.S. Pat. No. 4,718,421 improves upon this, by providing means for deformation that are actuated by pressurized agents instead of using mechanical adjustment. It is often desirable, however, to employ a locating system in combination with the acoustic wave source, in which case an opening preferably a central opening, must be provided for the component, such as an ultrasound scanner, which generates the locating field. Since the deformable lens wall in the aforementioned known system is executed as a flexible membrane, it is not possible without further complications to provide a central opening for the acceptance of the ultrasound head of an ultrasound locating systems.

SUMMARY OF THE INVENTION

It is an object of the present invention to provide an acoustic wave generator of the type having a liquid lens with a variable focal length, which is constructed in a simple and reliable way and which has a central opening for the acceptance of an ultrasound head belonging to an ultrasound locating system.

The above object is achieved in accordance with the principles of the present invention in an acoustic wave generator having a liquid lens with a central opening, formed by a rigid cylindrical inner wall and a deformable lens wall having an outer edge and an inner edge, with the outer edge of the deformable lens wall being fixed and the inner edge being displaceable by a means for deforming, the inner edge being displaceable in the direction of the center axis of the liquid lens in order to vary the focal length. The central opening can accept the ultrasound head of an ultrasound locating system. Since the inner edge of the deformable lens wall is displaceable, the dimensions of sealants whose resiliency allows an unimpeded deformation of the deformable lens wall can be kept optimally small.

A further advantage which is achieved is that, due to the displacement of the inner edge of the deformable lens wall, the volume of the liquid in the liquid lens as well as the volume of the acoustic propagation medium adjoining the deformable lens wall change far less when adjusting the focal length than would be the case given a dislocation of the outer edge of the deformable lens wall. Measures for compensating these volumes are thus simpler to design.

Another important advantage is that, given the displacement of the inner edge of the deformable lens wall, the changes in the peak pressure of the acoustic waves occurring in the focus of the acoustic waves, dependent on the focal length that is set, are far less than in the case of the displacement of the outer edge. The reason for this is that the substances employable as lens liquid usually highly acoustically attenuate acoustic waves and large changes in layer thickness of the lens liquid only occur in the radially inner region of the liquid lens when the inner edge is displaced, whereas these would occur in the radially outer region of the liquid lens if the outer edge of the deformable lens wall were displaced. In the invention, thus, a far smaller part of the acoustic waves must traverse the region of a large change in the layer thickness of the lens liquid, so that the influence of the variations in focal length on the peak pressure of the acoustic waves in the focus is only slight.

In an embodiment of the invention the seal between lens liquid and acoustic propagation medium in the region of the displaceable edge of the deformable lens wall preferably is made with a resiliently deformable sealant (for example, an accordion bellows or roll membrane) secured liquid-tight along the edge. As a result of this measure, the required deformation of the lens wall as well as the sealing of the lens liquid vis-a-vis the acoustic propagation medium can be realized in a simple way.

In a further embodiment of the invention, the means for deformation are actuated with a pressurized agent, whereby a liquid or a gas can be provided as the pressurized agent. As a consequence of the actuation with the pressurized agent, a simpler and more reliable structure is achieved when compared to mechanically actuated means. * In a preferred embodiment of the invention, the means for deformation are formed by a piston actuable with pressurized agent that is connected to the sealants.

* When actuating the means for deformation, the pressure of the pressurized agent can be as well positive as negative compared to ambient pressure.

In order to be able to compensate the volume fluctuations of the acoustic propagation medium and of the lens liquid occurring given variations in the focal length of the liquid lens, a volume compensating means is provided for the lens liquid and for the acoustic propagation medium in an embodiment of the invention. This, for example, can contain two compensating elements, for example reservoirs for the lens liquid and for the acoustic propagation medium that are independent of one another. The volume compensating means, however, can also be fashioned in the form of a single compensating volume subdivided liquid-tight into two, possible variable, sub-volumes for the lens liquid and for the acoustic propagation medium. The employment of volume compensating means, moreover, is fundamentally known from European Application 0 265 741, corresponding to U.S. Pat. No. 4,977,888 in conjunction with acoustic generators.

It is provided in another preferred embodiment of the invention that the volume compensating means for the lens liquid and the acoustic propagation medium each contain a volume, whereby the volumes are separated liquid-tight from one another, and that the means for deformation includes means for varying the volumes which, given a variation of the one volume, necessarily vary the other volume by the same amount in the opposite direction. The functions of the volume compensating means and of the means for deforming a lens wall can be realized in this way with greatly reduced structural outlay and avoiding the employment of a piston. Another simplification is achieved in an embodiment wherein the means for varying the volumes comprise a wall separating the volumes from one another, this wall being displaceable such that the volumes change in opposite directions. Accordion bellows are expediently provided for limiting the volumes.

DESCRIPTION OF THE PREFERRED EMBODIMENTS

Figure 1:
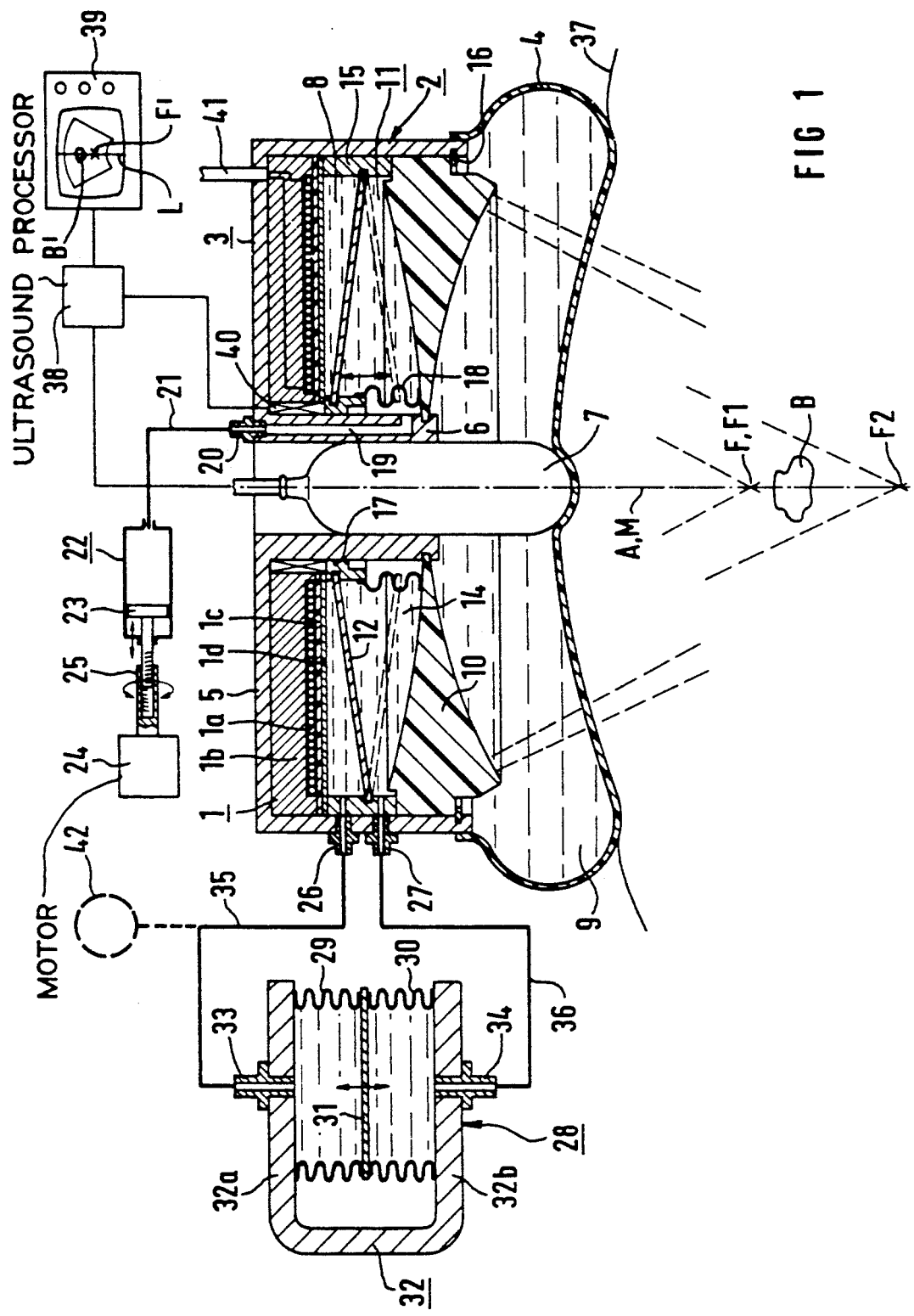
FIG. 1 is a longitudinal section through an acoustic wave generator constructed in accordance with the principles of the present invention shown schematically.

The generator of acoustic waves shown in FIG. 1 is a pressure pulse generator as employed in medicine, for example, for disintegrating calculi. The generator contains an electromagnetic pressure pulse source 1 and an acoustic positive lens allocated thereto which is generally referenced 2. The acoustic positive lens focuses the essentially planar pressure pulses emanating from the pressure pulse source 1 onto a focus F which, in practice, is a three-dimensional focal zone. Both are accepted in a housing 3 having an end remote from the pressure pulse source 1 closed liquid-tight with an elastic, flexible coupling cushion 4. The pressure pulse source 1, for example, may be an electromagnetic pressure pulse source as disclosed in European Application 0 188 750, corresponding to U.S. Pat. No. 4,697,588 and European Application 0 301 360, corresponding to U.S. Pat. No. 4,928,672. At its end neighboring the pressure pulse source 1, the housing 3 has a base 5 provided with a bore, with a tubular inside wall 6 extending from the bore in the direction toward the coupling cushion 4. The ultrasound applicator 7 of a known ultrasound locating system is accepted liquid-tight in the bore of the inside wall 6. The ultrasound applicator can be displaced along the center axis M of the generator in a known way and can be turned around this axis.

The space situated between the pressure pulse source 1 and the positive lens 2 is filled with water 8 and the space situated between the positive lens 2 and the coupling cushion 4 is filled with water 9, as the acoustic propagation medium.

The positive lens 2 is composed of a solid lens 10 and of a liquid lens generally referenced 11. The solid lens 2 is biconcavely shaped and is formed of a material, for example polystyrol, wherein the propagation speed of sound is higher than in the water 9 provided as the acoustic propagation medium. Consequently, the solid lens 10 acts as a positive lens. The inner edge of the annular solid lens 10 is introduced liquid-tight into a channel in the outer surface of the inner wall 6; the outer edge presses liquid-tight against the housing 3. The solid lens 10 has an outer circumference introduced liquid-tight into the housing 3.

The liquid lens 11 includes a lens liquid 14 between an entry wall 12 and the solid lens 10, the latter fulfilling the function of a plate-shaped, elastically deformable exit wall. The outer edge of the entry wall 12 formed, for example, of polymethylpentene (TPX) or polytetrafluoraethylene (PTFE), is accepted liquid-tight into a circumferential channel of a retainer ring 15. The retainer ring 15 is accepted axially non-displaceably between the pressure pulse source 1 and the solid lens 10, whereby the solid lens 10 is held axially non-dislocatable with a snap ring 16. The retainer ring has an outer surface pressed liquid-tight against the housing 3.

The inner circumferential edge of the entry wall 12 is accepted liquid-tight into a circumferential channel of an annular piston 17 disposed liquid-tight on the outer surface of the inner wall 6, and is displaceable thereon in the direction of the center axis M of the positive lens 2 and the liquid lens 11. Sealant not shown in FIG. 1 can be provided between the bore of the piston 17 and the outer generated surface of the inner wall 6.

The circumferential edge of an accordion bellows 18 is attached liquid-tight to the outer surface of the piston 17. The other circumferential edge of the accordion bellows 18 is attached liquid-tight to the solid lens 10 in the region of the inner edge thereof. The inner wall 6, the inner edge region of the solid lens 10, the piston 17 and the accordion bellows 18 thus limit an annular space into which an angled bore 19 discharges. Together with the solid lens 10, the entry wall 12, the retainer ring 15 and the piston 17, the accordion bellows 18 simultaneously limits the space of the liquid lens 11 that contains the lens liquid 14. A connecting sleeve 20 is introduced into the bore 19 thereby placing the bore 19 in fluid communication with a cylinder 22 via a line 21. This cylinder 22 contains a fluid, for example a liquid such as hydraulic oil, as a pressurized agent. The piston 23 of the cylinder can be moved back and forth with a schematically indicated electric motor 24 and a screw gearing 25 connected between the electric motor 24 and the piston rod of the piston 23 when the electric motor 24 is placed into rotation in the one or other direction. The movement of the piston 23 is transferred by the fluid onto the piston 17 which moves upward in the direction of the pressure pulse source 1 given a movement of the piston 23 toward the right and moves downward in the direction toward the solid lens 1 given a movement of the piston 23 toward the left. The focal length of the liquid lens 11 and, thus, the overall focal length of the positive lens 2 can be varied by deforming the entry wall 12 as a consequence of the displacement of the piston 17 between its two final positions.

When, as in the case of the illustrated exemplary embodiment, the lens liquid 14 a liquid wherein the speed of sound propagation is lower than in the water 8 provided as acoustic propagation medium (for example, Fluorinert ®, FC 75 ® or Flutec PP 3 ®), the liquid lens 11 acts as a positive lens for the final position shown with solid lines in FIG. 1. When the piston 17 is gradually displaced in the direction towards its other final position, the focusing effect of the liquid lens 11 is diminished and gradually changes into a slightly defocusing effect. The liquid lens 11 thus acts as a dispersing lens in the other final position-the position of the entry wall 12 is indicated with broken lines for this other final position. For the position of the focus F of the pressure pulses generated by the pressure pulse source 1 and focused with the positive lens 2, this means that the focus F1 situated closer to the pressure pulse source 1 is obtained for the final position of the piston shown with solid lines in FIG. 1 and the focus F2 at a greater distance therefrom derives for the final position indicated with broken lines. Dependent on the position of the piston 17, the focus F of the pressure pulses can be displaced with infinite variation along the acoustic axis A of the generator-which is identical with the center axis M-between these two final positions.

Since the volumes situated between the pressure pulse source 1 and the entry wall 12 and between the entry wall 12 and the solid lens 10 vary when the piston 17 is adjusted, schematically indicated connecting sleeves 26 and 27 are provided, which respectively place the volumes in fluid communication with a volume compensating unit generally referenced 28. The volume compensating unit 28 contains two accordion bellows 29 and 30 whose circumferential edges facing one another are soldered liquid-tight to a wall 31. The circumferential edges of the accordion bellows 29 and 30 remote from one another are soldered liquid-tight to respective legs 32a and 32b of a stiff U-shaped profile 32. Two connecting sleeves 33 and 34 that are respectively connected to the connecting sleeves 26 and 27 via schematically indicated lines 35 and 36 discharge into the two volumes formed in this manner. When displacing the piston 17, thus, the required volume compensation can ensue both with respect to the water 8 and with respect to the lens liquid 14, whereby the wall 31 displaces in accord with the movement of the piston 17.

For implementing a treatment, the generator together with its coupling cushion 4 are first pressed against the surface of the body 37 of a patient to be treated, this surface being schematically indicated in FIG. 1. Subsequently, the generator and the body 37 of the patient are aligned relative to one another with the assistance of the ultrasound applicator 7-which is preferably a B-scan applicator-such that the region B to be acoustically irradiated lies on the acoustic axis A of the generator. This is extremely easy when the ultrasound applicator 7 together with the ultrasound processor 38 generate an ultrasound image of a body slice containing the acoustic axis A on a monitor 39 with a line L indicating the position of the acoustic axis A being mixed into the image. A mark F', for example a cross-shaped mark, is also mixed into the ultrasound image, indicating the position of the focus F on the acoustic axis A. To this end, a position generator 40, for example a variable resistor, is connected to the piston 17 as schematically indicated in FIG. 1. The position generator 40 supplies a signal corresponding to the position of the piston 17 to the ultrasound means 38, the piston 17 in turn displacing the mark F' in the required way. In order to assure that the region B to be acoustically irradiated lies not only on the acoustic axis but also in the focus F of the pressure pulses, the electric motor 24 is actuated such that the mark F' coincides on the picture screen of the monitor 39 with the image B' of the region B to be acoustically irradiated. When this is the case, the region B to be acoustically irradiated can be charged with pressure pulses in the required way. Since the displacement path of the piston 23 is at least essentially proportional to the displacement path of the inner edge of the entry wall 12, there is also the possibility of providing a sensor, for example a potentiometer, instead of the position generator 40, which supplies a signal corresponding to the position of the piston 23, and thus indirectly corresponding to the position of the entry wall 12, to the ultrasound processor 38.

The pressure pulse source includes a flat coil 1a having helical turns arranged on the planar seating surface of a coil carrier 1b formed of insulating material and is separated from a planar, electrically conductive membrane 1d by an insulating foil 1c. The coil 1a is charged with high voltage pulses by a high-voltage pulse generator (not shown) and via a high-voltage cable 41 connected to the terminals of the flat coil 1a. As a consequence of the pulse-like current flowing through the flat coil 1a given a high-voltage pulse, the flat coil 1a quickly generates a magnetic field. This results in a current being induced in the membrane 1d, directed opposite the current flowing through the flat coil 1a. Since the magnetic field associated with the current flowing through the membrane 1d is also directed opposite the magnetic field associated with the current flowing through the flat coil 1a, the membrane 1d is suddenly repelled from the flat coil 1a. As a result, an essentially planar pressure pulse is introduced into the water 8, which is focused with the positive lens 2. The focused pressure pulse emerging from the positive lens 2 proceeds through the water 9 and the body tissue of the patient to the region B to be treated. The pressure pulse, moreover, gradually intensifies to form a shockwave on its way to the region to be treated. A shockwave as used herein means a pressure pulse having an extremely steep leading front.

In order to return the membrane 1d to its initial position after a pressure pulse has been generated-the membrane 1d lying flush against the flat coil 1 in this initial position with the insulating foil 1c therebetween-according to European Application 0 188 750 the side of the membrane 1d facing away from the flat coil 1a can be charged with under-pressure. It is alternatively possible to charge the water 8 situated between the membrane 1d and the entry wall 12 with a pressure elevated in comparison to the ambient pressure in order to return the membrane 1d into its initial position. This is indicated in broken lines in FIG. 1 in that an accumulator 42 is connected to the line 35. It is clear that means (not shown) can be provided that allow the height of the pressure with which the water 8 is charged to be set. In order to prevent the focal length of the positive lens 2 or of the liquid lens 11 from being deadjusted given pressure-charging of the water 8, it can be expedient under certain circumstances to provide a valve that allows the line 36 to be blocked during normal operation of the generator. Such a valve is only opened when a focal length adjustment of the positive lens 2 is to ensue.

Figure 2:
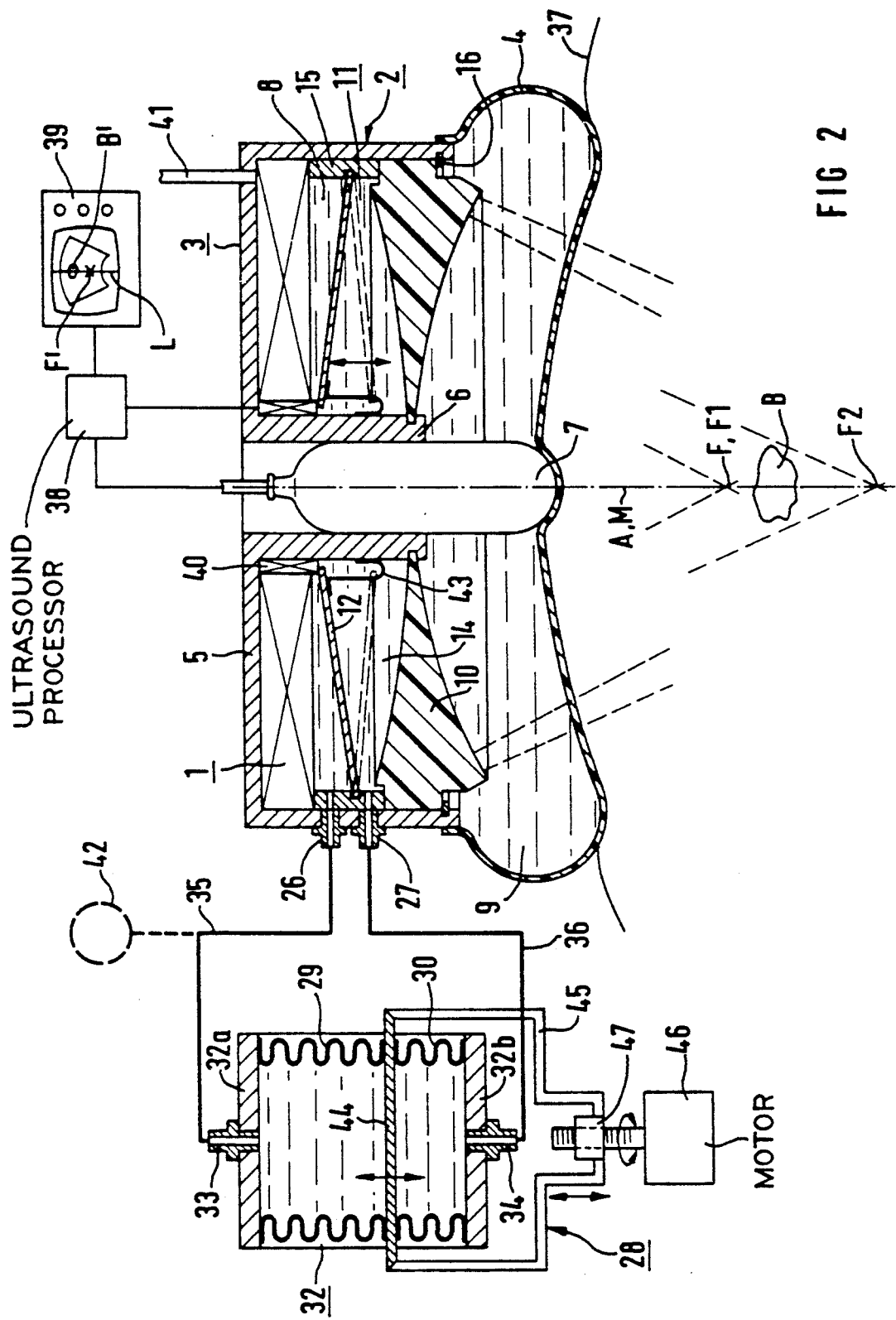
FIG. 2 is a schematic illustration of a longitudinal section through a further embodiment of an acoustic generator constructed in accordance with the principles of the present invention.

The embodiment shown in FIG. 2 agrees with that set forth above in terms of essential points, for which reason identical or similar parts respectively bear the same reference characters and the pressure pulse source 1 is not shown in detail.

A first important difference is that the parts 17 through 20 are omitted in the embodiment of FIG. 2. Instead, a roll membrane 43 is provided, with one end thereof being connected liquid-tight to the entry wall 12 and the other end thereof being connected liquid-tight to the inner edge region of the solid lens 10. The space containing the lens liquid 14 is separated liquid-tight from the space containing the water 8 in this way. The position generator 40 is directly connected to the entry wall 12 (in a way not shown in detail) and supplies a signal corresponding to the position of the inner edge of the entry wall 12.

The volume compensating unit 28 of FIG. 2 differs from that set forth above in that its two volumes are separated from one another by a rigid wall 44 to which a shackle 45 is attached, the shackle 45 being displaced back and forth in the longitudinal direction of the accordion bellows 29 and 30 with an electric motor 46 and a screw gearing 47, dependent on the direction in which the electric motor 46 turns. Consequently, the volumes are varied in a complementary manner, i.e., one of the volumes enlarges upon actuation of the electric motor 46 whereas the other is diminished to the same extent. As in the case of the exemplary embodiment set forth above, the entry wall 12 can consequently be adjusted with continuous variation between its final position shown with solid lines and its final position indicated with broken lines, resulting in displacement of the focus F of the pressure pulse between its two final positions F1 and F2. The roll membrane 43 is likewise shown with solid lines for the final position of the entry wall 12 shown with solid lines and is likewise shown with broken lines for the final position indicated with broken lines. The entry wall, moreover, moves downwardly away from the pressure pulse source 1 when the wall 44 is moved upwardly. Conversely, the entry wall 12 moves upwardly toward the pressure pulse source when the wall 44 is moved downwardly toward the electric motor 46.

Compared to the embodiment set forth above, the embodiment of FIG. 2 offers the advantage that a piston 17 can be foregone, this representing a considerable structural simplification since sealing problems, etc., are eliminated.

When, as in the case of the exemplary embodiment of FIG. 2, a charging of the water 8 with pressure elevated in comparison to ambient pressure is provided, a shut-off valve in the line 36 is not required, since a dislocation of the entry wall 12 is precluded. Such a displacement could only occur given a simultaneous occurrence of a displacement of the wall 44. Such a displacement, however, can only occur given actuation of the electric motor 46.

The acoustic positive lens in the two described exemplary embodiments is a combination of a solid lens 10 and a liquid lens 11, whereby the solid lens 10 simultaneously forms one of the lens walls of the liquid lens 11. However, it is also fundamentally possible to provide only a liquid lens. In this case, there is the possibility of executing both lens walls in deformable fashion and to allocate means for deformation to both lens walls. A greater range of adjustment for the focus of the pressure pulses can be realized on the basis of this measure.

Both exemplary embodiments share the above-explained advantages in view of smaller changes in the volume of the lens liquid contained in the liquid lens 11 and of the volume of the acoustic propagation medium situated between the deformable lens wall 12 and the pressure pulse source 1 as well as in view of smaller changes in the peak pressure of the pressure pulses in the focus F given a change in focal length.

The invention has been set forth above with reference to the example of a pressure pulse generator that contains an electromagnetic pressure pulse source. The invention, however, can also be employed in combination with pressure pulse sources that contain pressure pulse sources acting in a different way, for example piezoelectrically. In the case of the described exemplary embodiment, the generator of the invention is employed for a medical purpose. However, it can also be utilized for any other desired medical and non-medical purposes. Moreover, there is also the possibility of inventively fashioning other generators of acoustic waves, for example ultrasound generators that serve therapeutic, diagnostic or other purposes.

Although modifications and changes may be suggested by those skilled in the art, it is the intention of the inventor to embody within the patent warranted hereon all changes and modifications as reasonably and properly come within the scope of his contribution to the art.

I claim as my invention:

1. An acoustic wave generator comprising:
    a housing containing an acoustic propagation medium;
    means for generating acoustic waves propagating in a propagation direction in said acoustic propagation medium;
    a liquid lens for focusing said acoustic waves, said liquid lens being disposed in said acoustic propagation medium and having two spaced lens walls disposed at least substantially transversely to said propagation direction and lens liquid between said two lens walls, said two lens walls and said lens liquid, in combination, defining a focal length of said liquid lens;
    said liquid lens having a central opening extending in said propagation direction formed by an inner wall, with said two lens walls each having an inner edge proximate said inner wall and an outer edge remote from said inner wall;
    the inner edge of at least one of said lens walls being movable along said inner wall and the outer edge of said at least one lens wall being fixed; and
    means for deforming said at least one lens wall by moving said inner edge thereof along said inner wall for varying the focal length of said liquid lens.

2. An acoustic wave generator as claimed in claim 1 further comprising a resiliently deformable sealing means, disposed between said inner wall and said inner edge of said at least one lens wall, for maintaining a seal between said lens liquid and said acoustic propagation medium.

3. An acoustic wave generator as claimed in claim 1 wherein said means for deforming is a means for causing a pressurized agent to interact with said at least one lens wall for deforming said at least one lens wall.

4. An acoustic wave generator as claimed in claim 3 further comprising a resiliently deformable sealing element, disposed between said inner wall and said inner edge of said at least one lens wall, and wherein said means for deforming is a means for causing said pressurized agent to interact with said at least one lens wall to expand and compress said sealing element.

5. An acoustic wave generator as claimed in claim 1 wherein the deformation of said at least one lens wall causes displacement of said lens liquid and said acoustic propagation medium, and further comprising means for compensating for said displacement of said lens liquid and said acoustic propagation medium.

6. An acoustic wave generator as claimed in claim 1 wherein said at least one lens wall is disposed with said lens liquid on one side thereof and said acoustic propagation medium on an opposite side thereof, and wherein said means for deforming is a means for varying the respective volumes of said lens liquid and said acoustic propagation medium in a complementary manner by increasing one of said volumes while simultaneously decreasing the other of said volumes.

7. An acoustic wave generator as claimed in claim 6 further comprising volume compensating means for accommodating overflow from the volume reduced by said means for deforming.

8. An acoustic wave generator as claimed in claim 7 wherein said volume compensating means includes a first chamber for said lens liquid and a second chamber for said acoustic propagation medium, said first and second chambers being separated liquid-tight from each other.

9. An acoustic wave generator as claimed in claim 6 wherein said means for varying the respective volumes of said lens liquid and said acoustic propagation medium comprises a container in fluid communication with said acoustic propagation medium in said housing and said lens liquid in said liquid lens and containing a portion of said acoustic propagation medium and a portion of said lens liquid, and having a displaceable wall separating said lens liquid and said acoustic propagation in said container from each other, and means for displacing said wall to vary said volumes in a complementary manner.

10. An acoustic wave generator as claimed in claim 9 wherein said container is formed by an accordion bellows.

11. An acoustic wave generator as claimed in claim 1 wherein said means for deforming comprises a piston, a pressurized agent, and means for causing said pressurized agent to interact with said piston for deforming said at least one lens wall.

* * * * *